United States Patent
Seybold et al.

(10) Patent No.: US 10,238,293 B2
(45) Date of Patent: Mar. 26, 2019

(54) VIEWING GRID AND IMAGE DISPLAY FOR VIEWING AND RECORDING SKIN IMAGES

(71) Applicant: DermSpectra LLC, Tucson, AZ (US)

(72) Inventors: Karleen Seybold, Tucson, AZ (US); Karim Alami, San Diego, CA (US); Brian Lau, Anaheim, CA (US); Clara Curiel, Tucson, AZ (US)

(73) Assignee: DermSpectra LLC, Tucson, AZ (US)

( * ) Notice: Subject to any disclaimer, the term of this patent is extended or adjusted under 35 U.S.C. 154(b) by 4 days.

(21) Appl. No.: 14/860,509

(22) Filed: Sep. 21, 2015

(65) Prior Publication Data
US 2016/0081554 A1    Mar. 24, 2016

Related U.S. Application Data (60) Provisional application No. 62/053,027, filed on Sep. 19, 2014.

(51) Int. Cl.
*H04N 7/18* (2006.01)
*A61B 5/00* (2006.01)
*G06F 19/00* (2018.01)
*G16H 10/60* (2018.01)

(52) U.S. Cl.
CPC ........... *A61B 5/0077* (2013.01); *A61B 5/441* (2013.01); *A61B 5/7425* (2013.01); *G06F 19/321* (2013.01); *G16H 10/60* (2018.01); *A61B 5/0013* (2013.01); *A61B 5/4842* (2013.01)

(58) Field of Classification Search
CPC .............................. G06F 19/321; G16H 10/60
USPC ........................................................... 348/77
See application file for complete search history.

(56) References Cited

U.S. PATENT DOCUMENTS

| | | | |
|---|---|---|---|
| 2002/0000998 A1* | 1/2002 | Scott | G06F 17/30274 345/667 |
| 2004/0116813 A1* | 6/2004 | Selzer | A61B 5/02007 600/467 |
| 2012/0257072 A1* | 10/2012 | Jirman | G06T 11/00 348/222.1 |
| 2014/0226003 A1* | 8/2014 | Phaneuf | H01J 37/222 348/80 |
| 2014/0333959 A1* | 11/2014 | Casas | G06F 19/321 358/1.15 |

* cited by examiner

*Primary Examiner* — Richard T Torrente
(74) *Attorney, Agent, or Firm* — Zeman-Mullen & Ford, LLP (57) ABSTRACT

A viewing navigation grid and imaging display especially useful for viewing recorded skin images.

13 Claims, 9 Drawing Sheets

VIEWING GRID AND IMAGE DISPLAY FOR VIEWING AND RECORDING SKIN IMAGES

CROSS-REFERENCE TO RELATED APPLICATIONS

This application claims priority to provisional patent application having Ser. No. 62/053,027, filed Sep. 19, 2014, which is herein incorporated by reference in its entirety, and is related to patent application having Ser. No. 13/778,942, filed Feb. 27, 2013, and patent application having Ser. No. 13/781,735, filed Feb. 28, 2013, both of which are also herein incorporated by reference in their entireties.

FIELD OF INVENTION

The present invention is directed to a viewing navigation grid and imaging display especially useful for viewing and recording skin images. More particularly, the present invention is directed to a system and method for viewing and recording skin images which includes a device for capturing a plurality of overlapping skin images, a server for storing and transmitting patient images and patient information, at least one of a computer and/or a mobile computing device in communication with the server, and a processor configured to be in communication with a program application that places a grid on top of a body image of the patient to create a human body navigational grid having sections that can be selected and magnified to further view in more detail an area of skin contained within the selected section of the navigational grid. The system may further include a reduced size image of the human body navigational grid displayed on a magnified image of a selected section of the navigational grid to guide a viewer on where they are in the patient's body.

BACKGROUND OF THE INVENTION

Although several methods and apparatus exist in the prior art for imaging and recording a patient's skin, the present invention was created to efficiently, effectively, and easily display skin images and identify and record observations relating to those skin images including skin abnormalities and areas of concern. The present invention was also created to easily make side by side image comparisons of the same areas of the skin taken at different times and to enable sharing of those displayed images, compared images, and recorded observations relating to those images with patients, health care workers, and health care related entities.

SUMMARY OF THE INVENTION

The present invention is directed to a system and method for viewing and recording skin images. One exemplary embodiment of the system of the present invention for viewing and recording skin images includes a device for capturing a plurality of overlapping skin images of a patient, a server for storing and transmitting patient images and patient information, at least one computer and/or a mobile computing device in communication with the server, and a processor configured to be in communication with a program application that places a grid on top of a body image created from the plurality of overlapping skin images or a body image selected from the plurality of overlapping skin images of the patient to create a human body navigational grid having sections that can be selected and magnified by a viewer or health care worker to further view an area of skin contained within the selected section of the navigational grid in more detail. The program application of the system may further include a reduced size image of the human body navigational grid displayed on a magnified image of a selected section of the navigational grid that has been selected by a viewer or healthcare worker to view in more detail. This allows the viewer or healthcare worker to determine where they are looking on the patient's body. In one exemplary embodiment, the reduced size navigational grid is displayed in the lower right side of the magnified selected section image of the navigational grid.

In another exemplary embodiment, the program application may include one or more boundary configurations that can be used to draw a boundary around an area of concern identified on the area of skin contained within the magnified selected section of the navigational grid. The boundary configuration may be a square, a circle, or a free form line with no particular geometry that is drawn around the area of concern to highlight the area of concern.

In still another exemplary embodiment of the system of the present invention, the program application may include the ability to select one or more categories that identify which body part contains the area of concern and areas of the body part where the area of concern is located as well as the ability for a viewer or healthcare worker to record notes and/or observations relating to the area of concern. The viewer or healthcare worker may also be able to record a diagnosis and/or a medical code relating to the area of concern.

In yet another exemplary embodiment of the system of the present invention for viewing and recording skin images, the program application may include the ability to compare the area of concern with previous recorded images of the same area of concern to enable a side by side comparison of the area of concern taken at different times. The program application of the system of the present invention may also include the ability to share images of concern with the patient, other healthcare professionals, and/or health care related entities via a wired and/or wireless connection.

One exemplary embodiment of the method of the present invention for viewing and recording skin images includes the steps of obtaining a plurality of overlapping images of a patient, creating a body image from the overlapping images of the patient or selecting one of the overlapping images of the patient as a body image, placing a grid on top of the body image to create a human body navigational grid having sections that can be selected and magnified to further observe an area of skin in more detail, placing a reduced size image of the human body navigational grid on a selected and magnified section of the human body navigational grid to guide a viewer on where they are on the patient's body, and recording an area of concern on the patient's skin by drawing a boundary around the area of concern contained within the selected and magnified section of the human body navigational grid. The boundary drawn around the area of concern may include a number of configurations including, but not limited to, a square, a circle, or a free form line having no particular geometry. In one exemplary embodiment, the reduced size image of the human body navigational grid may be displayed in a lower right side of the selected and magnified section of the human body navigational grid.

In another exemplary embodiment, the method of the present invention may also include the step of selecting and recording one or more categories that identify which body part contains the area of concern and areas of the body part where the area of concern is located and/or the step of recording notes and/or observations relating to the area of concern. The method may also include the step of identifying and recording a diagnosis and/or medical code relating to the area of concern.

In still another exemplary embodiment, the method of the present invention for viewing and recording skin images may include the step of comparing the area of concern with previous recorded images of the same area of concern to enable a side by side comparison of the area of concern taken at different times. The method of the present invention may also include the step of sharing the image(s) of concern with the patient, other healthcare workers, and/or health care related entities via a wired or wireless connection.

BRIEF DESCRIPTION OF THE DRAWINGS

The subject invention will hereinafter be described in conjunction with the appended drawing figures which depict exemplary screen shots of a graphical user interface (GUI) seen by a physician/healthcare worker while viewing skin care images of a patient, identifying and recording areas of concern on the images, and comparing the images to skin images that were previously taken of the same areas on the patient, and where.

DETAILED DESCRIPTION OF EXEMPLARY EMBODIMENTS

The system for viewing and recording skin images of the present invention is generally directed to exemplary embodiments which include a device for capturing a plurality of overlapping skin images of a patient, a server for storing and transmitting patient images and patient information, one or more computers and/or mobile computing devices that are in communication with the server, and a processor configured to be in communication with a program application that places a grid on top of a body image of a patient to create a human body navigational grid having sections that can be selected and magnified by a healthcare worker to further view an area of skin in more detail that is contained within the selected section of the navigational grid. Although there are many devices capable of capturing a plurality of overlapping skin images of a person/patient, some exemplary embodiments of such a device can be found in patent application having Ser. No. 13/778,942 which is herein incorporated by reference in its entirety. Further, although there are many examples of servers and processors capable of being in communication with program applications, some exemplary embodiments of such elements can be found in patent application having Ser. No. 13/781,735 which is herein incorporated by reference in its entirety. It will be understood by those skilled in the art that although exemplary embodiments of some of the functional elements included in the present invention can be found in these cited pending applications, many other similar elements may be used in the present invention to assist in providing the unique viewing and recording features that make the system and method of the present invention novel. It should also be noted that the body image of the patient used to create the human body navigational grid of the present invention may be created from processing a plurality of overlapping images taken of the patient or may be created from one selected image taken of the patient.

Figure 1:
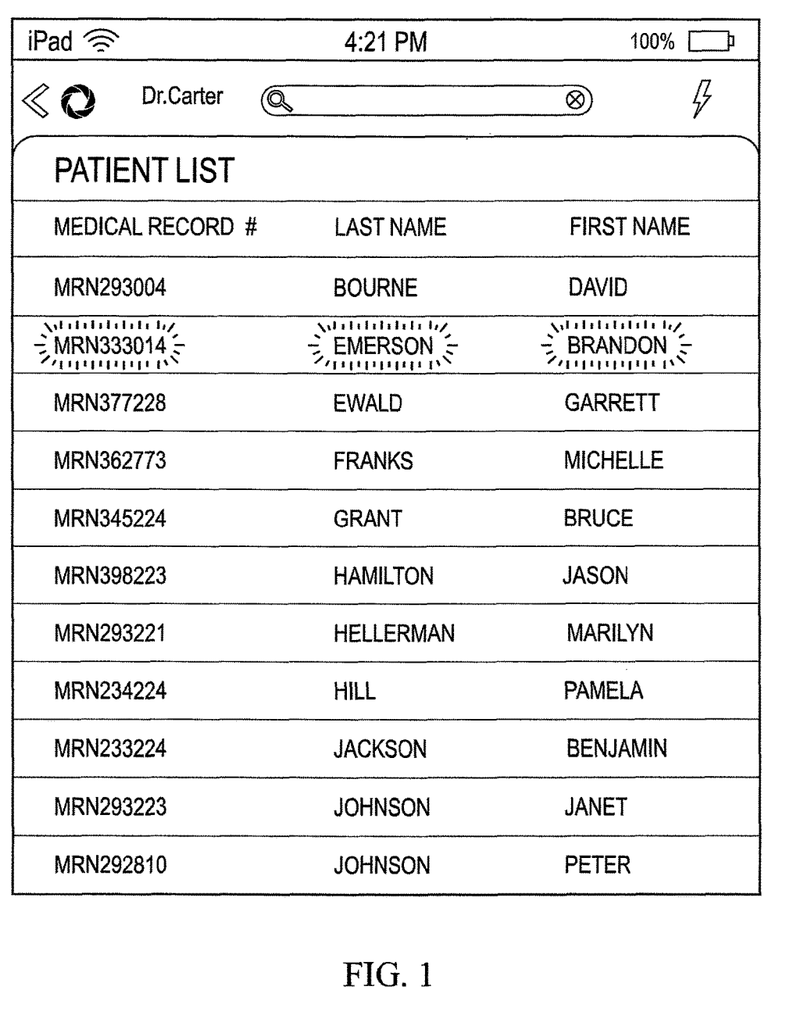
FIG. 1 is a GUI screen shot showing a patient list that can be accessed to select a patient that has had multiple images of themselves taken with one or more cameras.
Figure 2:
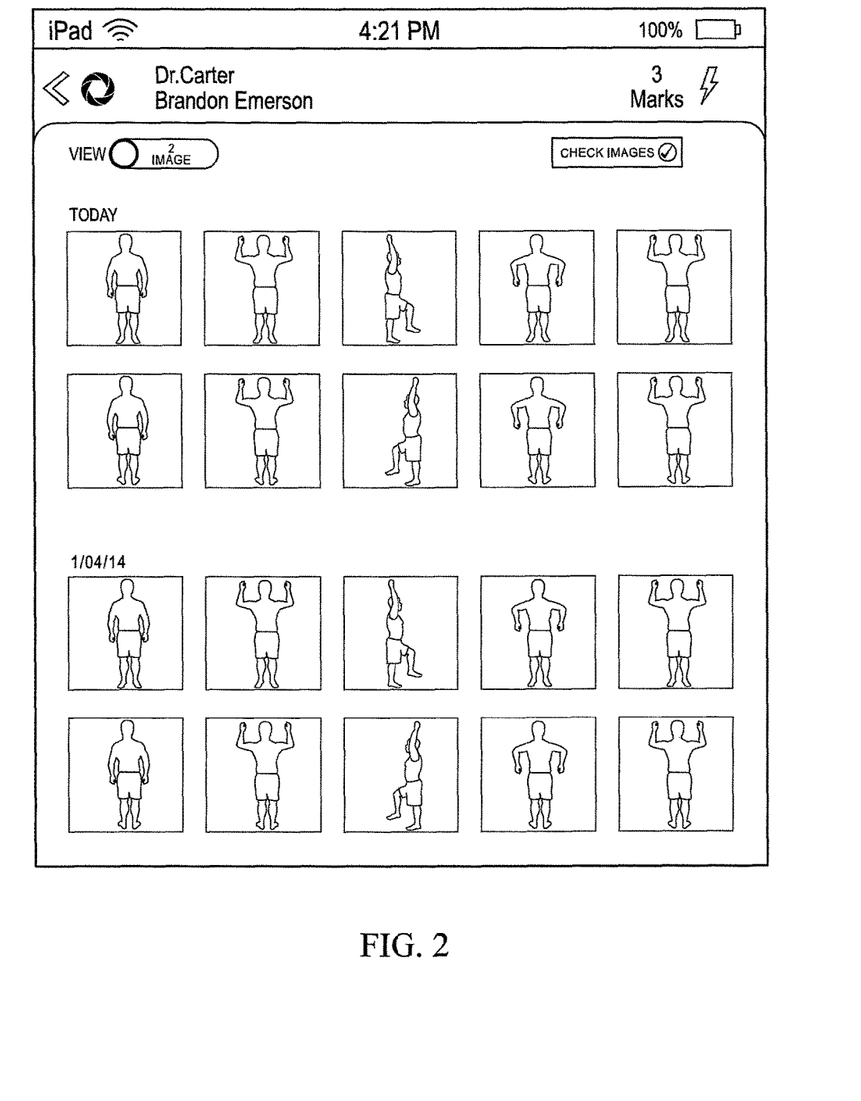
FIG. 2 is a GUI screen shot showing images of a patient in multiple poses to ensure that images of all areas of the patient's skin are obtained.
Figure 3:
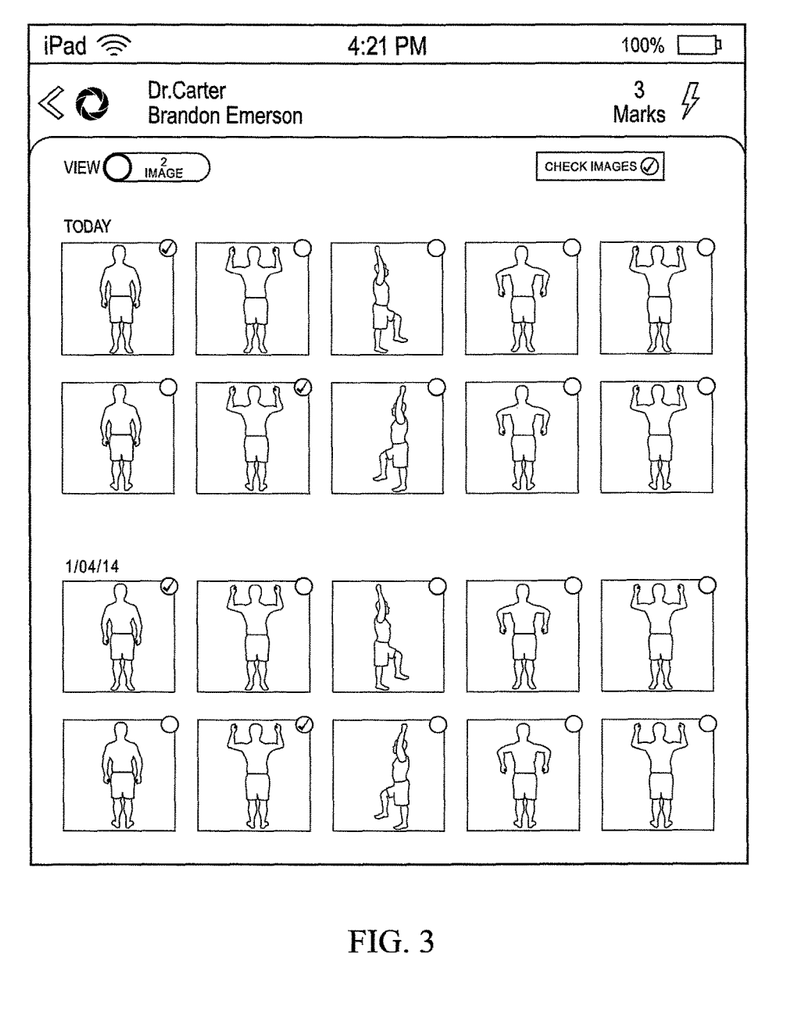
FIG. 3 is a GUI screen shot showing how a physician or healthcare worker can select specific images to view in more detail.

FIG. 1 is a GUI screen shot showing a patient list that can be accessed to select a patient that has had multiple images of themselves taken with one or more cameras. The starburst type dashes around the third entry on the patent list indicate the patient that is being selected for viewing and recording of skin images. FIG. 2 is a GUI screen shot showing images of the selected patient in multiple poses to ensure that images of all areas of the patient's skin are obtained. FIG. 2 also shows that the same set of poses were undertaken by the patient on two different dates to obtain two different sets of images of the same patient. FIG. 3 is a GUI screen shot showing that a physician or healthcare worker has selected two images from each set of images that were taken on different dates where the images selected show the same poses. Selection is shown by making a checkmark in the upper right hand corner of the image. These images have been chosen by the physician/healthcare worker so that they can view those images in more detail.

Figure 4:
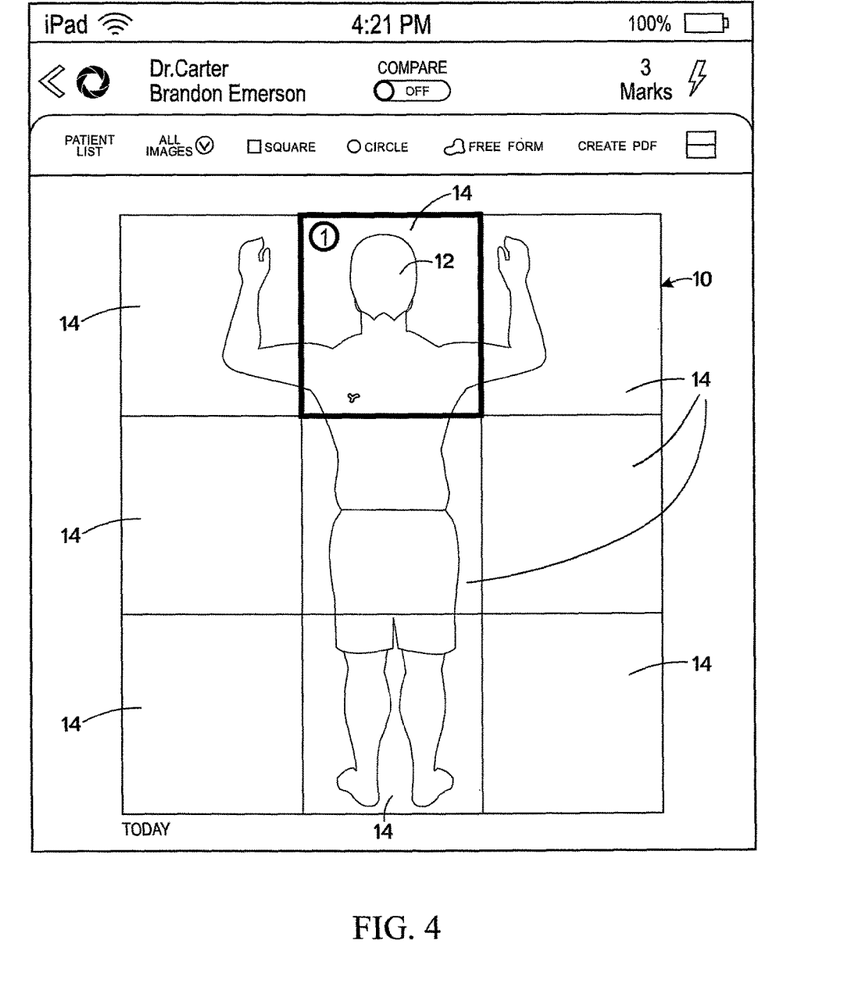
FIG. 4 is a GUI screen shot of a human body navigational grid of a patient that was created by placing a grid on top of a body image of the patient where the body image could be created from processing overlapping images of the body or from selecting one image from the overlapping images of the body and the ability to select a section of the human body navigational grid to further view that area of skin of the patient in more detail.

FIG. 4 is a GUI screen shot of a human body navigational grid 10 of a patient 12 that was created by placing a grid on top of a body image of the patient where the body image was created from processing overlapping images of the body or from selecting one image from the overlapping images of the body. This exemplary embodiment of the human body navigational grid 10 has nine separate sections 14 but it will be understood by those skilled in the art that any number of sections may be used to create the human body navigational grid 10. FIG. 4 also shows that one of the sections 14 of the human body navigational grid 10 has been selected for further detailed examination as indicated by the section 14 numbered "1" inside a circle in the upper left hand corner of the section.

Figure 5:
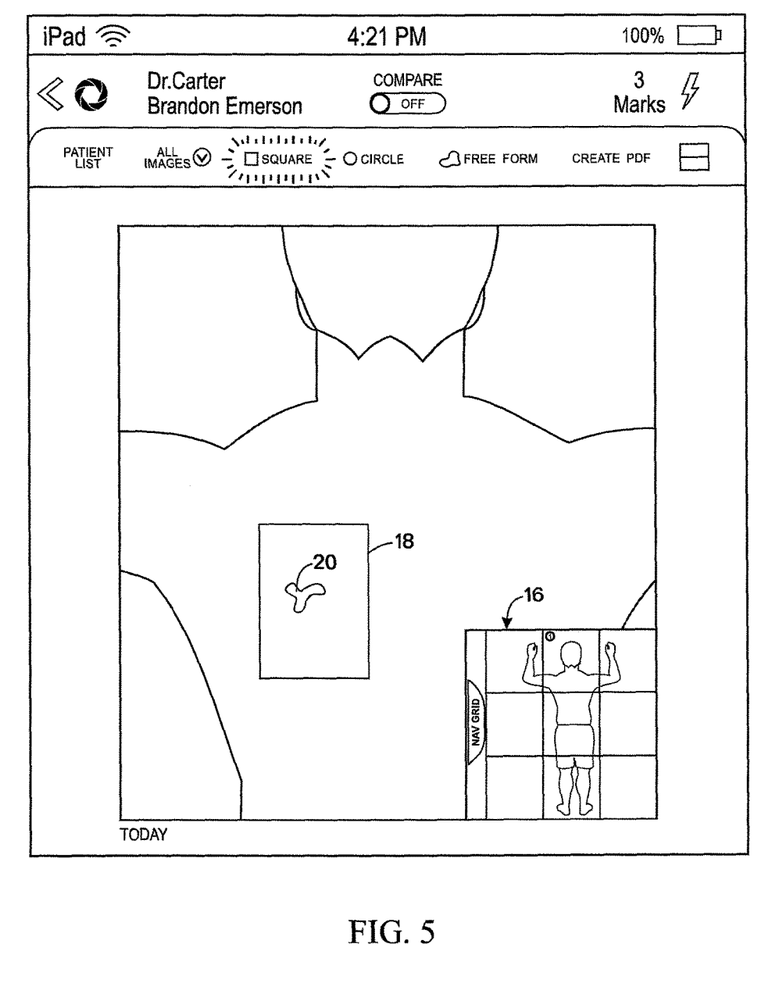
FIG. 5 is a GUI screen shot showing a magnified view of the section of the human body navigational grid selected in FIG. 4 with a reduced size image of the human body navigational grid displayed on the bottom right hand side of the magnified view and a square boundary drawn around a potential area of concern on the magnified image of the patient's skin.
Figure 6:
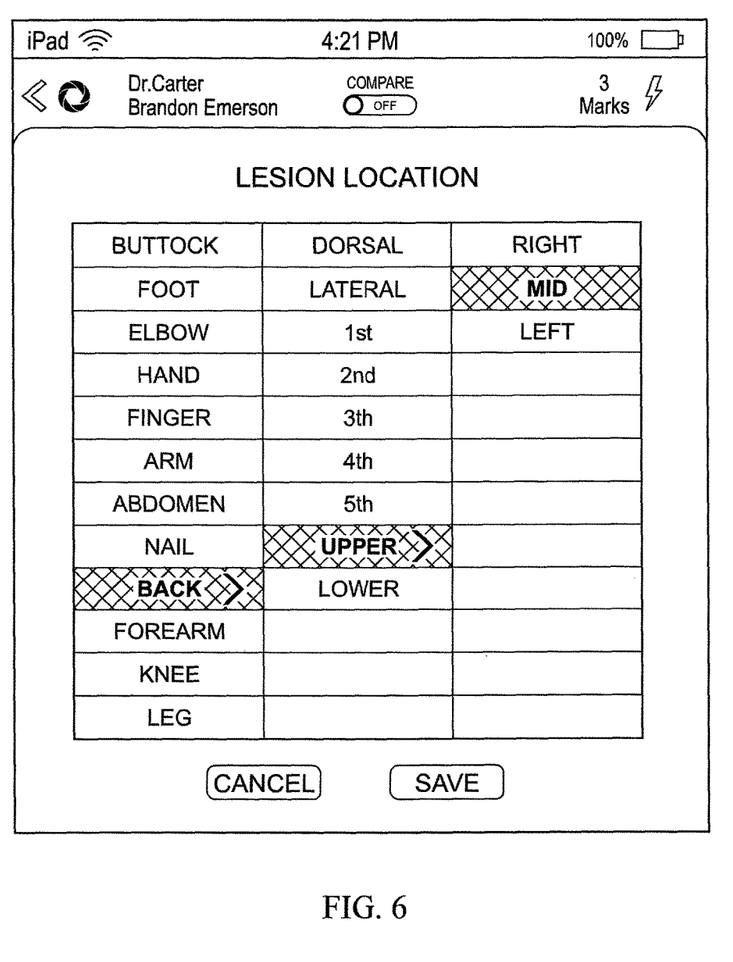
FIG. 6 is a GUI screen shot showing categories that can be selected to identify which body part contains the area of concern and areas of the body part where the area of concern is located.
Figure 7:
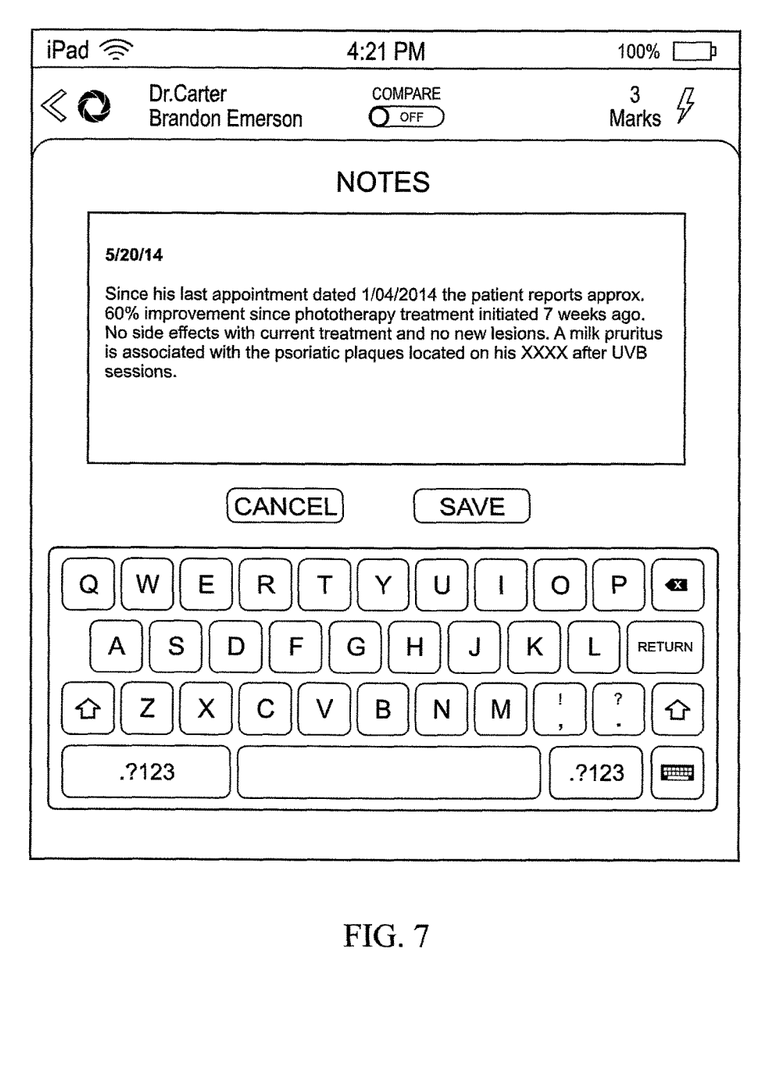
FIG. 7 is a GUI screen shot showing an area where a healthcare worker can record notes relating to an identified area of concern.

FIG. 5 is a GUI screen shot showing a magnified view of the section 14 (indicated by the section numbered "1" inside a circle) of the human body navigational grid 10 selected in FIG. 4 with a reduced size image 16 of the human body navigational grid displayed on the bottom right hand side of the magnified view and a square boundary 18 drawn around a potential area of concern on the magnified image of the patient's skin. The reduced size image 16 of the navigational grid is shown on the magnified view of section 14 to assist the viewer in determining what part of the patient's body they are viewing. As further shown in FIG. 5, sunburst type dashes around the square icon and the term "square" at the top of the screen indicate that a square configuration has been selected to create a boundary around an area of concern 20 that is seen on the patient's skin. It will be noted that other boundary configurations such as a circle and free form are also available for creating the boundary around the area of concern on the patient's skin. A GUI screen shot showing categories that can be selected to identify which body part contains the area of concern and areas of the body part where the area of concern is located is shown in FIG. 6. The hatched categories represent the categories that were selected to identify the body part that contains the area of concern 20 shown in FIG. 5. Categories selected are "Back" for body part and "Upper" and "Mid" for location on the body part. FIG. 7 is a GUI screen shot showing an area where a physician/healthcare worker can record notes relating to the identified area of concern 20.

Figure 8:
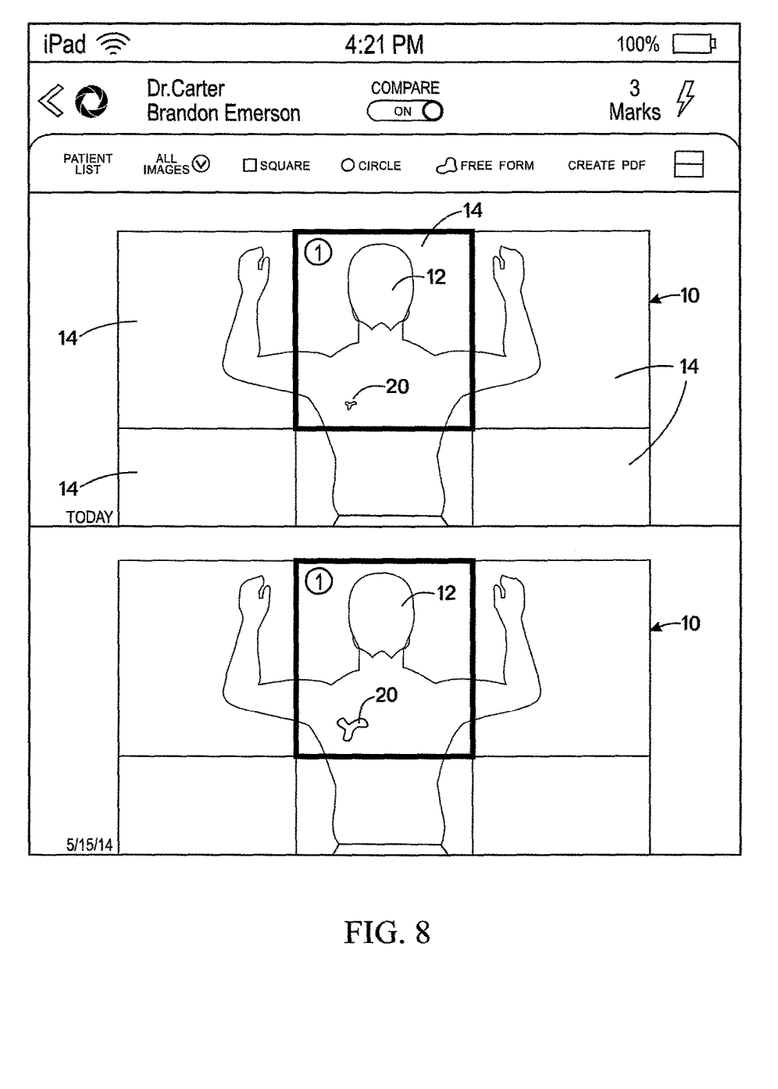
FIG. 8 is a GUI screen shot comparing an identified area of concern with a previous recorded image of the same area of concern taken on a different date.
Figure 9:
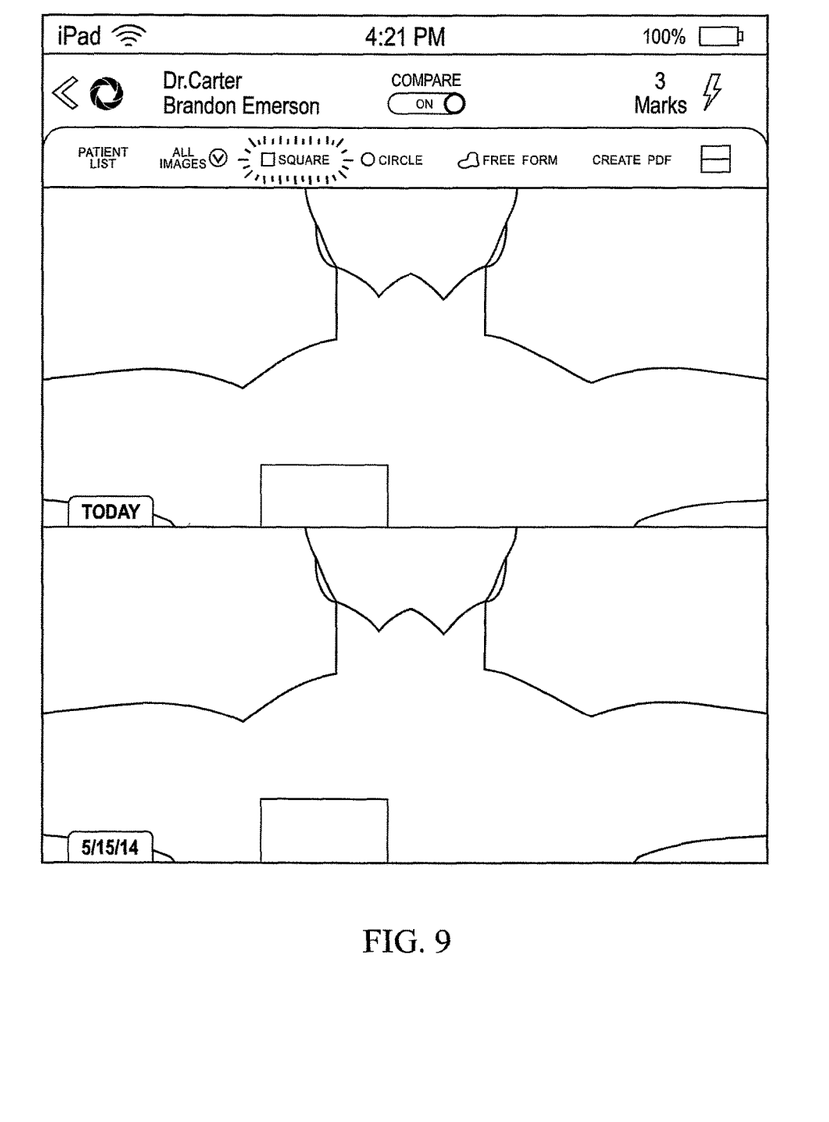
FIG. 9 is a GUI screen shot showing a magnified version of the screen shot shown in FIG. 8.

FIG. 8 is a GUI screen shot comparing part of the human body navigational grid 10 containing an identified area of concern 20 with a previous recorded image of the same area of concern 20 taken on a different date. This comparison shows that the area of concern 20 has gotten smaller since the date of the previously recorded image. FIG. 9 is a GUI screen shot showing a magnified area of the screen shot shown in FIG. 8. It will be understood by those skilled in the art that any section of the human body navigational grid may be selected and magnified at any number of magnifications necessary to enable a physician/healthcare worker to observe the details of the skin shown in the image.

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning. It should be noted that the terms "physician" and "healthcare worker" and "viewer" are used interchangeably throughout and are not meant to be limiting in any way.

The invention claimed is:

1. A system for viewing and recording skin images comprising:
   a device for capturing a plurality of overlapping images of a patient;
   a server for storing and transmitting patient images and patient information;
   at least one of a computer and/or a mobile computing device in communication with the server; and
   a processor configured to be in communication with a program application that places a grid on top of a total body image created from the plurality of overlapping images of a patient to create a total human body navigational grid having sections that can be selected and magnified by a health care worker to further view an area of skin contained within the selected section of the total human body navigational grid in more detail wherein a reduced size image of the total human body navigational grid is displayed on the magnified image of the selected section of the total human body navigational grid that has been selected by the healthcare worker to view in more detail and wherein the program application further includes one or more boundary configurations that can be used to draw a boundary around an area of concern identified on the area of skin contained within the magnified selected section of the total human body navigational grid, an ability to select one or more written categories that identify which body part contains the area of concern and areas of the body part where the area of concern is located, and an ability to compare the area of concern with previous recorded images of the same area of concern to enable a side by side comparison of the area of concern taken at different times.

2. The system of claim 1 wherein the reduced size image of the total human body navigational grid is displayed in a lower right side of the magnified selected section image of the total human body navigational grid.

3. The system of claim 1 wherein the boundary configuration may comprise at least one of a square, a circle, and a free form not specific to a particular geometry.

4. The system of claim 1 wherein the program application further includes an ability for a healthcare worker to record notes and/or observations relating to the area of concern.

5. The system of claim 1 wherein the program application further includes an ability for a healthcare worker to record at least one of a diagnosis and a medical code relating to the area of concern.

6. The system of claim 1 wherein the program application includes the ability to share the images of concern with the patient, other healthcare professionals, and/or health care related entities via a wired and/or wireless connection.

7. A method for viewing and recording skin images comprising the steps of:
   obtaining a plurality of overlapping images of a patient;
   creating a total body image from the overlapping images of the patient;
   placing a grid on top of the total body image to create a total human body navigational grid having sections that can be selected and magnified to further observe an area of skin in more detail;
   placing a reduced size image of the total human body navigational grid on a selected and magnified section of the total human body navigational grid to guide a viewer on where they are in the patient's body;
   recording an area of concern on the patient's skin by drawing a boundary around the area of concern contained within the selected and magnified section of the total human body navigational grid;

selecting and recording one or more written categories that identify which body part contains the area of concern and areas of the body part where the area of concern is located; and comparing the area of concern with previous recorded images of the same area of concern to enable a side by side comparison of the area of concern taken at different times.

8. The method of claim 7 wherein the boundary drawn around the area of concern comprises at least one of a square, a circle, and a free form having no particular geometry.

9. The method of claim 7 wherein the reduced size image of the total human body navigational grid is displayed in a lower right side of the selected and magnified section of the total human body navigational grid.

10. The method of claim 7 further comprising the step of recording notes and/or observations relating to the area of concern.

11. The method of claim 7 further comprising the step of identifying and recording at least one of a diagnosis and a medical code relating to the area of concern.

12. The method of claim 7 further comprising the step of sharing the images of concern with the patient, other healthcare professionals, and/or health care related entities via a wired and/or wireless connection.

13. The method of claim 7 further comprising the step of sharing the area of concern with the patient, other healthcare professionals, and/or health care related entities via a wired and/or wireless connection.

* * * * *